(12) United States Patent
Adiri et al.

(10) Patent No.: US 9,972,077 B2
(45) Date of Patent: May 15, 2018

(54) METHOD AND SYSTEM FOR AUTOMATED VISUAL ANALYSIS OF A DIPSTICK USING STANDARD USER EQUIPMENT

(71) Applicant: HEALTHY.IO LTD, Tel Aviv (IL)

(72) Inventors: Yonatan Adiri, Tel Aviv (IL); Ido Omer, Ramat Hasharon (IL); Shachar Mendelowitz, Tel Aviv (IL); Roee Salomon, Tel Aviv (IL)

(73) Assignee: HEALTHY.IO LTD., Tel Aviv (IL)

( * ) Notice: Subject to any disclaimer, the term of this patent is extended or adjusted under 35 U.S.C. 154(b) by 378 days.

(21) Appl. No.: 14/274,817

(22) Filed: May 12, 2014

(65) Prior Publication Data

US 2015/0325006 A1 Nov. 12, 2015

(51) Int. Cl.
*G06T 7/90* (2017.01)
*G06T 5/00* (2006.01)
(Continued)

(52) U.S. Cl.
CPC ............ *G06T 5/007* (2013.01); *G06K 9/2027* (2013.01); *G06K 9/4652* (2013.01);
(Continued)

(58) Field of Classification Search
CPC ......... G06T 5/007; G06T 7/0012; G06T 7/90; G06T 2207/30072; G06T 2207/10024;
(Continued)

(56) References Cited

U.S. PATENT DOCUMENTS 4,523,852 A * 6/1985 Bauer ........................ G01J 3/52
356/243.5
7,652,268 B2 1/2010 Patel
(Continued)

FOREIGN PATENT DOCUMENTS

WO WO2012131386 10/2012
WO WO2013077802 5/2013
(Continued)

OTHER PUBLICATIONS

Shen, Li, Joshua A. Hagen, and Ian Papautsky. "Point-of-care colorimetric detection with a smartphone." Lab on a Chip 12, No. 21 (2012): 4240-4243.*
(Continued)

*Primary Examiner* — Siamak Harandi
*Assistant Examiner* — Carol Wang
(74) *Attorney, Agent, or Firm* — Pearl Cohen Zedek; Latzer Baratz LLP

(57) ABSTRACT

A method and system for automated visual analysis of a dipstick using standard user equipment (UE) are disclosed herein. The method may include the following steps: capturing, using an arbitrary UE having specified image capturing and processing capabilities, an image of a dipstick having colored test reagents, and a calibration array having a plurality of colored calibration elements which are tailored specifically to the test reagents; deriving, based on the captured image, illumination parameters associated with the dipstick and the calibration array; determining whether the illumination parameters are within predefined illumination boundary conditions sufficient for interpreting the test reagents, given the specified image capturing and processing capabilities of the UE; applying image enhancement operations to the captured image, based on predefined mapping between the derived illumination parameters and the required adjustments; and interpreting the colored test reagents, based on the colored calibration elements, in the enhanced captured image.

23 Claims, 3 Drawing Sheets

(51) Int. Cl.
- *G06K 9/46* (2006.01)
- *G06K 9/20* (2006.01)
- *G06T 7/00* (2017.01)

(52) U.S. Cl.
CPC .......... *G06K 9/4661* (2013.01); *G06T 7/0012* (2013.01); *G06T 7/90* (2017.01); *G06K 2009/4666* (2013.01); *G06T 2207/10024* (2013.01); *G06T 2207/30004* (2013.01); *G06T 2207/30072* (2013.01)

(58) Field of Classification Search
CPC ........ G06T 2207/30004; G06K 9/2027; G06K 9/4652; G06K 9/4661; G06K 2009/4666
See application file for complete search history.

(56) References Cited

U.S. PATENT DOCUMENTS

| | | | | |
|---|---|---|---|---|
| 8,877,140 | B2 | 11/2014 | Chen | |
| 2007/0024657 | A1* | 2/2007 | Zhang | H04N 1/6033 347/19 |
| 2012/0063652 | A1* | 3/2012 | Chen | G01N 21/274 382/128 |
| 2013/0267032 | A1* | 10/2013 | Tsai | G01N 21/78 436/95 |
| 2014/0072189 | A1* | 3/2014 | Jena | G01N 21/8483 382/128 |
| 2015/0055134 | A1 | 2/2015 | Papautsky | |
| 2015/0211987 | A1* | 7/2015 | Burg | G01N 35/00029 356/402 |
| 2015/0278575 | A1* | 10/2015 | Allano | G06K 9/00127 382/133 |

FOREIGN PATENT DOCUMENTS

| | | |
|---|---|---|
| WO | WO 2013/116831 | 8/2013 |
| WO | WO2014025415 | 2/2014 |

OTHER PUBLICATIONS

International search report for PCT application No. PCT/IL2015/050487 dated Sep. 16, 2015.
European Search Report dated Oct. 10, 2017 for corresponding European Application No. 15792976.1.
Office Action dated Sep. 7, 2017 from U.S. Appl. No. 15/050,710.
Loh B.Y., N.K. Vuong et al; "Automated Mobile pH Reader on a camera phone"; IAENG International Journal of Computer Science, vol. 38, No. 3 (2011): pp. 268-274.
Vuong N.K., et al; "Classification of pH levels using a mobile phone." In Consumer Electronics 2009. ISCE 09. IEEE 13th International Symposium on, pp. 823-827. IEEE, 2009.
Filippini Daniel, et al; "Measurment strategy and instrumental performance of a computer screen photoassisted technique for the evaluation of a multi-parameter colorimetric test strip". Analyst, vol. 131, No. 1 (2006): pp. 111-117.

* cited by examiner

METHOD AND SYSTEM FOR AUTOMATED VISUAL ANALYSIS OF A DIPSTICK USING STANDARD USER EQUIPMENT

FIELD OF THE INVENTION

The present invention relates generally to systems and methods of automatically analyzing dipsticks, and in particular to such methods implementing image processing techniques tailored for standard user equipment.

BACKGROUND OF THE INVENTION

Prior to setting forth a short discussion of the related art, it may be helpful to set forth definitions of certain terms that will be used hereinafter.

The term "user equipment" (UE) refers herein to any device used directly by an end-user to communicate. It can be a hand-held telephone, a laptop computer equipped with a mobile broadband adapter, or any other device. In the context used herein UE refers specifically to an arbitrary platform which is equipped with image capturing, image processing, and wireless communication capabilities.

The term "testing dipstick" or simply "dipstick" refers herein to a testing measurement device usually made of paper or cardboard and is impregnated with reagents that indicate some feature of a liquid or a gas by changing color. In medicine, dipsticks can be used to test for a variety of liquids for the presence of a given substance, known as an analyte. For example, urine dipsticks are used to determine properties of a given sample and detect and measure the presence of a variety of substances that indicate a person's state of health.

The term "specularity" refers herein to the visual appearance of specular reflection. In computer vision, it means the mirror like properties of the surface: A directional reflection of incoming light (illumination) as described by the law of reflection. A simplified modelling of that reflection is the specular component in the Phong reflection model.

Dipsticks are used by a variety of healthcare providers to assist in diagnostics, specifically, but not exclusively of urinary analysis of patients. The core concept is a set of reagents which are designed to chemically react to substances in a liquid under test (e.g., urine) by changing their color within a predefined color range. The set of colored reagents can then be compared to a predefined color key which can be used, either manually (e.g., by an expert user) or automatically (e.g., using a dedicated image processing computerized system) to yield qualitative and quantitative data relating to the substances in the liquid under test.

Currently, image processing can be used to interpret the color reagent responses into quantitative and qualitative clinical data. This is being carried out by dedicated hardware which may include a pre-calibrated scanner, which is operated in well-known and monitored illumination conditions, and a classifier that operates based on the calibrated images derived by the scanner.

The need to use dedicated hardware necessitates patients carry out the dipstick test in clinics rather than in the convenience of their home or other place of choice. Such a visit to the lab also mandates coming in unnecessary contact with infections and diseases. A non-expert interpretation of the dipstick is also not recommended—for the fear of wrong interpretation and misdiagnosis. It would be therefore be advantageous to be able to produce such accurate clinical data at home, using image processing techniques, without the need to use a dedicated hardware or software.

SUMMARY OF THE INVENTION

Embodiments of the present invention overcome the aforementioned disadvantages of the prior art by enabling a non-expert user to carry out computerized, automatic interpretation of a dipstick, using a standard arbitrary platform at his or her location of choice.

According to one embodiment of the present invention, there is provided a method of visual analysis of a dipstick using user equipment having optical capturing and image processing capabilities. The method may include the following steps: capturing, through a user equipment (UE) having specified image capturing and processing capabilities, an image of a dipstick having one or more colored test reagents, and a calibration array having a plurality of colored calibration elements, tailored specifically for the dipstick color reagents; deriving, based on the captured image, illumination parameters associated with the dipstick and the calibration array; determining whether the illumination parameters are within predefined illumination boundary conditions which are sufficient for interpreting the one or more colored test reagents, given the specified image capturing and processing capabilities of the UE; applying one or more image enhancement operations on the captured image, based on predefined mappings between the derived illumination parameters and one or more required adjustments; and interpreting the one or more colored test reagents, based on the colored calibration elements, in the enhanced captured image. Advantageously, by embodiments of the present invention, the dipstick-specific calibrator can, in real time, determine whether the environment of choice crosses boundary conditions.

These additional, and/or other aspects and/or advantages of the present invention are set forth in the detailed description which follows.

BRIEF DESCRIPTION OF THE DRAWINGS

For a better understanding of the invention and in order to show how it may be implemented, references are made, purely by way of example, to the accompanying drawings in which like numerals designate corresponding elements or sections. In the accompanying drawings.

Examples illustrative of embodiments of the invention are described below with reference to the figures attached hereto. In the figures, identical structures, elements or parts that appear in more than one figure are generally labeled with the same number in all the figures in which they appear. Dimensions of components and features shown in the figures are generally chosen for convenience and clarity of presentation and are not necessarily shown to scale.

Figure 1:
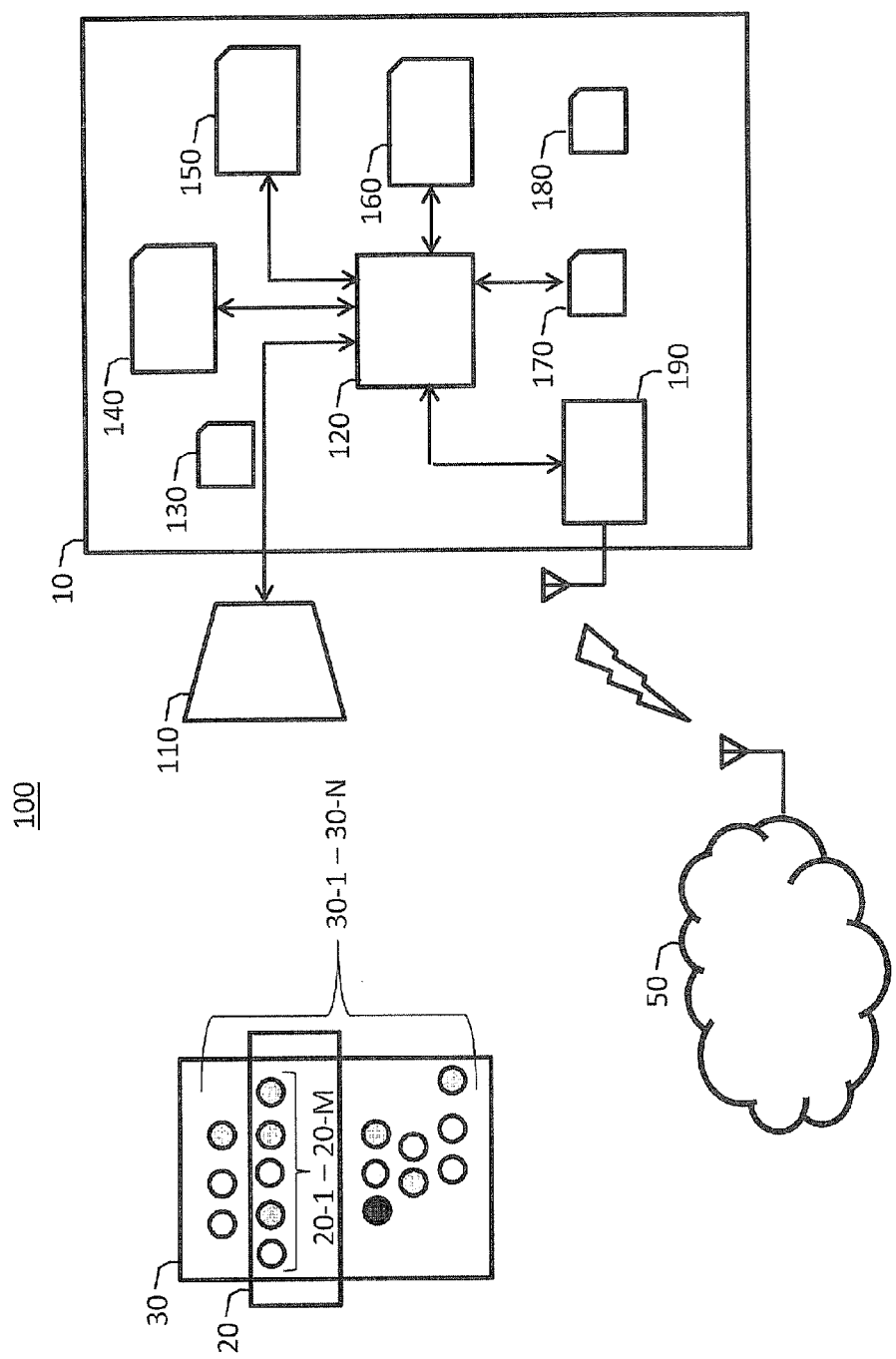
FIG. 1 is a high level schematic block diagram illustrating a system according to the present invention.

The drawings together with the following detailed description make the embodiments of the invention apparent to those skilled in the art.

DETAILED DESCRIPTION OF THE INVENTION

With specific reference now to the drawings in detail, it is stressed that the particulars shown are for the purpose of example and solely for discussing the preferred embodiments of the present invention, and are presented in the cause of providing what is believed to be the most useful and readily understood description of the principles and conceptual aspects of the invention. In this regard, no attempt is made to show structural details of the invention in more detail than is necessary for a fundamental understanding of the invention. The description taken with the drawings makes apparent to those skilled in the art how the several forms of the invention may be embodied in practice.

Before explaining the embodiments of the invention in detail, it is to be understood that the invention is not limited in its application to the details of construction and the arrangement of the components set forth in the following descriptions or illustrated in the drawings. The invention is applicable to other embodiments or of being practiced or carried out in various ways. Also, it is to be understood that the phraseology and terminology employed herein is for the purpose of description and should not be regarded as limiting.

FIG. 1 is a high level schematic block diagram illustrating a system 100 according to embodiments of the present invention. System 100 may include an arbitrary platform 10 such as user equipment (UE) having an image capturing device 110 having specified image capturing and a computer processor 120 processing capabilities. Capturing device 110 may be configured to capture one or more images of a dipstick 20 having one or more colored test reagents 20-1 to 20-M, and a pre-generated calibrator 30 (referred herein also as a calibration array) having a plurality of colored calibration elements 30-1 to 30-N. Calibration elements 30-1 to 30-N are tailored specifically for the dipstick color reagents, and are generated specifically for each type of dipstick based on its properties it is understood that a single calibrator may be tailored for a plurality of dipsticks, as long as it is tailored to a group of dipsticks and not all possible dipsticks.

Computer processor 120 may be configured to: derive, based on the captured image 130, illumination parameters 140 associated with the dipstick and the calibration array. Computer processor 120 may further be configured to determine whether the illumination and other parameters such as the spatial angle of the UE relative to the calibration array are within predefined illumination boundary conditions 150 which are sufficient for interpreting the one or more colored test reagents, given the specified image capturing and processing capabilities of arbitrary platform (or UE) 10.

In some embodiments of the present invention, computer processor 120 may further be configured to apply one or more image enhancement operation 160 on the captured image, wherein the image enhancement operation 160 is configured for rendering the color reagents at captured image more distinguishable and less prone to artifacts; and interpret the one or more colored test reagents, based on the colored calibration setup, in the enhanced captured image 170.

In an alternative embodiment, aforementioned enhancement operation 160 may be carried on a location remote to arbitrary platform 10 such as one or more servers on a cloud network 50, to which arbitrary platform 10 may be connected, e.g., by a Wi-Fi connection using communication circuitry 190. In a case wireless connection is not available; the data may be stored on UE 10 and transmitted later to cloud 50 once wireless connectivity is resumed.

According to some embodiments of the invention, in a case that the illumination parameters are not within the predefined illumination boundary conditions, instructing a user of the arbitrary platform with instructions 180 how to improve the illumination parameters.

According to some embodiments of the invention, the one or more image enhancement operation may include detecting portions of specular reflections coming from the colored calibration shapes or the colored test reagents, and applying image processing algorithms that reduce the specular reflections.

According to some embodiments of the invention, the one or more image enhancement operation comprises determining, for each pixel at the captured image associated with one of the colored test reagents, a uniform color, based on a normalization factor calculated based on the derived illumination parameters and the specified image capturing and processing capabilities.

According to some embodiments of the invention, in a case that the illumination parameters are not within the predefined illumination boundary conditions, indicating to a user that interpreting of the dipstick by the arbitrary platform is not possible.

According to some embodiments of the invention, wherein the one or more colored test reagents, and the colored calibration elements are located, based on a specified layout, in prearranged locations.

According to some embodiments of the invention, the instruction to the user indicate a specified movement pattern of the arbitrary platform vis à vis the dipstick and the calibration array.

According to some embodiments of the invention, the detecting of portions of specular reflections is carried out by comparing pixels associated with a same color reagent, to a predefined threshold.

Figure 2:
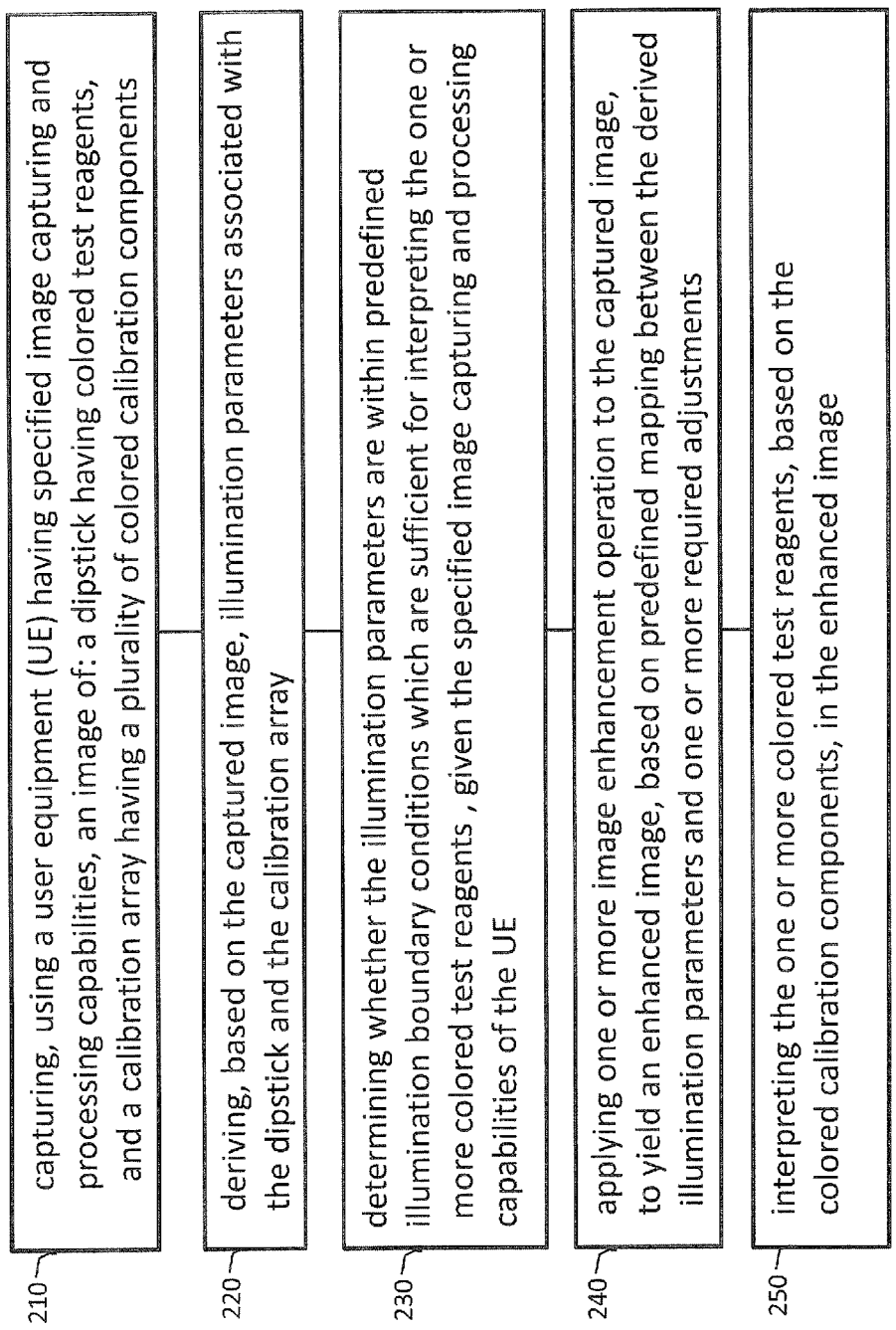
FIG. 2 is a high level flowchart diagram illustrating an aspect of a method according to some embodiments of the present invention.

FIG. 2 is a high level flowchart diagram illustrating an aspect of a method 200 according to some embodiments of the present invention. The method may include the following steps: capturing, using an arbitrary platform having specified image capturing and processing capabilities, an image of: a dipstick having one or more colored test reagents, and a calibration array having a plurality of colored calibration elements which are specifically tailored to the test reagents of the dipstick 210; deriving, based on the captured image, illumination parameters associated with the dipstick and the calibration array 220; determining whether the illumination parameters are within a predefined illumination boundary conditions which is sufficient for interpreting the one or more colored test reagents, given the specified image capturing and processing capabilities of the arbitrary platform 230; applying one or more image enhancement operation on the captured image, based on predefined mapping between the derived illumination parameters and one or more required adjustments 240; and interpreting the one or more colored test reagents, based on the colored calibration elements, in the enhanced captured image 250. It is understood that, while implementing method 200 may be carried out using the aforementioned architecture of system 100, other architectures may be used by those skilled in the art.

Figure 3:
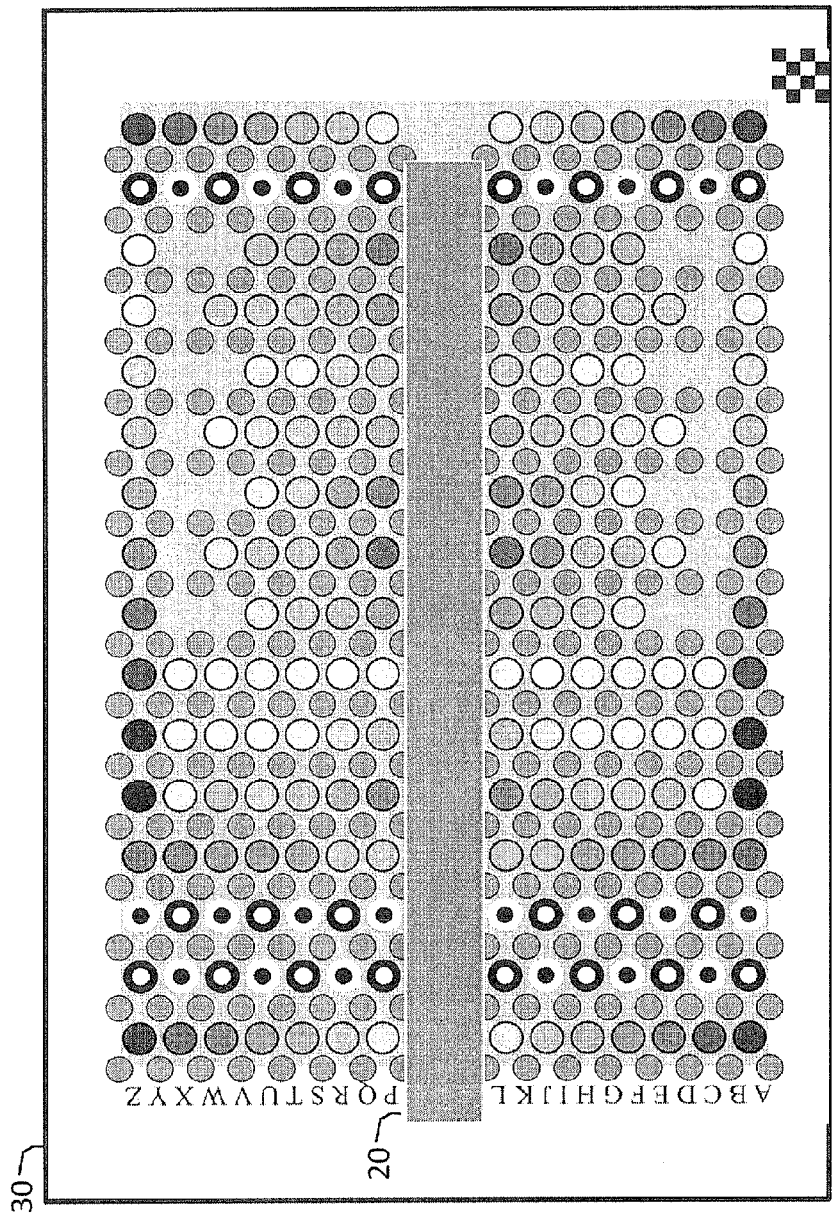
FIG. 3 is an exemplary non-limiting calibration array illustrating an aspect of some embodiments of the present invention.

FIG. 3 is an exemplary non limiting embodiment of a calibration array 30 exhibiting a plurality of calibration elements and a designated location for dipstick 20. Calibration array may be pre-generated after a long process of learning the myriads of illumination conditions that may be presented when capturing the image using the arbitrary platform (UE). The calibration elements are carefully tailored per each type of dipstick for optimal performance. Additionally, the different capturing capabilities of many platforms (e.g., smart telephones, tablet PC and the like) are being studied. All of the above is being carefully used in embodiments of the present invention in order to produce dipstick-specific calibrators that have a very large dynamic range in the sense that many illumination conditions are within the operation boundary of the capturing process that is sufficient for proper interpretation of the medical data on the dipstick. The calibration elements of calibrator 30 shown in FIG. 3 have been carefully selected to have different shades of basic colors, several textures and positions relative to dipstick 20.

According to some embodiments, calibrator 30 may be provided with a texture for matching or rectification and base colors for on the fly normalization. Additionally, the calibrator may apply a reverse effect of the response function of the capturing device of the arbitrary platform 10. In some embodiments, a representative response function is assumed. In others, different calibrators are used for groups of known arbitrary platforms.

According to other embodiments, the calibrator is provided with arbitrary geometrical elements for simplifying dipstick extraction (when dipstick 20 has rectangular reagents), and exhibiting more gray levels for improved gamma correction.

According to other embodiments, the calibrator is provided with calibration elements using two reference elements per color for a better normalization and specularity identification.

According to other embodiments, calibrator 30 is provided with calibration elements having black borders around them for minimizing over smoothing of certain colors by some camera models. Additionally, uniform gray arbitrary geometrical elements may be are added for better normalization (again, due to over smoothing). Adding high contrast circular elements for enabling fast blob based calibrator rectification on the phone.

As will be appreciated by one skilled in the art, the aforementioned process of generating the calibration may be the product of trial and error process that can be implemented in various manners. It should be noted that the aforementioned guidelines may be used in order to generate further improvements for the calibration.

Aspects of the present invention may be embodied as a system, method or an apparatus. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system, and a "cloud".

The aforementioned flowchart and block diagrams illustrate the architecture, functionality, and operation of possible implementations of systems and methods according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A method comprising: capturing, using a capturing device of a standard user equipment (UE) having specified image capturing and processing capabilities, an image of a dipstick having one or more colored test reagents, positioned on a calibration array having a plurality of colored calibration elements, and uniform gray arbitrary geometrical elements, wherein said plurality of sets of colored calibration elements reflects a plurality of: illumination conditions, capturing capabilities of potential UEs and response functions of capturing devices of the potential UEs, wherein each of the sets is specifically tailored to span a color gamut of a respective one of said colored test reagents; deriving, based on the colored calibration elements and the uniform gray arbitrary geometrical elements in the captured image, local illumination parameters associated with the captured image of the dipstick and the calibration array; applying one or more image enhancement operation to the captured image, to yield an enhanced image, based on predefined mapping between the derived local illumination parameters and one or more required adjustments; normalizing illumination of the captured image based on the local illumination parameters; and interpreting the one or more colored test reagents, based on the normalized illumination and the colored calibration elements, in the enhanced image.

2. The method according to claim 1, further comprising, in a case that the illumination parameters are not within a set of predefined illumination boundary, instructing a user of the UE how to improve the illumination parameters.

3. The method according to claim 2, wherein the instruction to the user indicate a specified movement pattern of the UE vis à vis the dipstick and the calibration array.

4. The method according to claim 1, wherein the one or more image enhancement operations comprises detecting portions of specular reflections coming from the colored calibration elements or the colored test reagents, and applying image processing algorithms that reduces the specular reflections.

5. The method according to claim 4, wherein the detecting of portions of specular reflections is carried out by comparing pixels associated with a same color element or reagent, to a predefined threshold.

6. The method according to claim 1, wherein the one or more image enhancement operation comprises normalizing a color of each pixel of each reagent, to yield, a uniform color, based on a normalization factor calculated based on the derived illumination parameters and the specified image capturing and processing capabilities.

7. The method according to claim 1, wherein the one or more image enhancement operation comprises normalizing a color of each pixel of each reagent and calibration elements to achieve uniform illumination.

8. The method according to claim 1, further comprising, in a case that the illumination parameters are not within a predefined illumination boundary, indicating to a user that a proper interpreting of the dipstick by the arbitrary platform is not possible.

9. The method according to claim 1, wherein the one or more colored test reagents, and the colored calibration elements are located, based on a specified layout, in prearranged locations.

10. The method according to claim 1, wherein the calibration array is generated based on data derived in a series of trials and error, in which a plurality of illumination conditions were tested against a plurality of UEs.

11. The method according to claim 1, wherein at least one of: shape, color, location, and texture of the calibration elements on the calibration array are selected in an optimization process, configured to increase likelihood of a successful interpretation of the colored test reagents.

12. A system comprising: a user equipment (UE) having specified image capturing and processing capabilities, configured to capture, using an image capturing device, an image of a dipstick having one or more colored test reagents, positioned on a calibration array having a plurality of colored calibration elements and uniform gray arbitrary geometrical elements, wherein said plurality of sets of colored calibration elements reflects a plurality of: illumination conditions, capturing capabilities of potential UEs and response functions of capturing devices of the potential UEs, wherein each of the sets is specifically tailored to span a color gamut of a respective one of said colored test reagents; and a computer processor configured to: derive, based on the colored calibration elements and the uniform gray arbitrary geometrical elements in the captured image, local illumination parameters associated with the captured image of the dipstick and the calibration array; apply one or more image enhancement operation to the captured image, to yield an enhanced image, based on predefined mapping between the derived local illumination parameters and one or more required adjustments; normalize illumination of the captured image based on the local illumination parameters; and interpret the one or more colored test reagents, based on the normalized illumination parameters and the colored calibration elements, in the enhanced captured image.

13. The system according to claim 12, wherein the computer processor is further configured, in a case that the illumination parameters are not within a predefined illumination boundary, to instruct a user of the arbitrary platform how to improve the illumination parameters.

14. The system according to claim 13, wherein the instruction to the user indicate a specified movement pattern of the arbitrary platform visa vis the dipstick and the calibration array.

15. The system according to claim 12, wherein the one or more image enhancement operation comprises detecting portions of specular reflections coming from the colored calibration elements or the colored test reagents, and applying image processing algorithms that reduces the specular reflections.

16. The system according to claim 15, wherein the detecting of portions of specular reflections is carried out by comparing pixels associated with a same color reagent, to a predefined threshold.

17. The system according to claim 12, wherein the one or more image enhancement operation comprises determining, for each pixel at the captured image associated with one of the colored test reagents, a uniform color, based on a normalization factor calculated based on the derived illumination parameters and the specified image capturing and processing capabilities.

18. The system according to claim 12, wherein the one or more image enhancement operation comprises normalizing the pixel colors of the reagent and calibration elements to achieve uniform illumination.

19. The system according to claim 12, wherein the computer processor is further configured, in a case that the illumination parameters are not within a predefined illumination boundary, to indicate to a user that interpreting of the dipstick by the arbitrary platform is not possible.

20. The system according to claim 12, wherein the one or more colored test reagents, and the colored calibration elements are located, based on a specified layout, in prearranged locations.

21. The system according to claim 12, wherein the calibration array is generated based on data derived in a series of trial and error, in which a plurality of illumination conditions were tested.

22. The system according to claim 12, wherein at least one of: shape, color, location, and texture of the calibration elements on the calibration array are selected in an optimization process, configured to increase likelihood of a successful interpretation of the colored test reagents.

23. A computer program product comprising: a non-transitory computer readable storage medium having a computer readable program embodied therewith, the computer readable program comprising: a computer readable program configured to instruct a user equipment (UE) having specified image capturing and processing capabilities, to capture an image of a dipstick having one or more colored test reagents, positioned on a calibration array having a plurality of colored calibration elements, and uniform gray arbitrary geometrical elements, wherein said plurality of sets of colored calibration elements reflects a plurality of: illumination conditions, capturing capabilities of potential UEs and response functions of capturing devices of the potential UEs, wherein each of said plurality of sets of colored calibration elements are specifically tailored to span a color gamut of a respective one of said colored test reagents; a computer readable program configured to derive, based on the colored calibration elements and the uniform gray arbitrary geometrical elements in the captured image, local illumination parameters associated with the captured image of the dipstick and the calibration array; a computer readable program configured to determine whether the local illumination parameters are within a predefined illumination boundary which is sufficient for interpreting the one or more colored test reagents, given the specified image capturing and processing capabilities of the UE; a computer readable program configured to apply one or more image enhancement operation to the captured image, to yield an enhanced image, based on predefined mapping between the derived local illumination parameters and one or more required adjustments; a computer readable program configured to normalize illumination of the captured image based on the local illumination parameters; and a computer readable program configured to interpret the one or more colored test reagents, based on the normalized illumination parameters and the colored calibration elements, in the enhanced image.

* * * * *